US005480416A

United States Patent [19]
Garcia et al.

[11] Patent Number: 5,480,416
[45] Date of Patent: Jan. 2, 1996

[54] CARDIAC PACEMAKER WITH UNIVERSAL COATING

[75] Inventors: John Garcia, Houston, Tex.; Eckhard Alt, Ottobrunn, Germany; Lawrence J. Stotts, Lake Jackson, Tex.

[73] Assignee: Intermedics, Inc., Angleton, Tex.

[21] Appl. No.: 310,570

[22] Filed: Sep. 22, 1994

[51] Int. Cl.⁶ .................................................. A61N 1/05
[52] U.S. Cl. ............................ 607/36; 607/116; 128/642
[58] Field of Search .............................. 607/36, 37, 116, 607/119; 128/642

[56] References Cited

U.S. PATENT DOCUMENTS

| | | | |
|---|---|---|---|
| 4,310,000 | 1/1982 | Lindemans | 607/36 |
| 4,369,791 | 1/1983 | Friedman | 607/36 |
| 5,314,430 | 5/1994 | Bardy | 607/36 |
| 5,388,578 | 2/1995 | Yomtov et al. | 607/37 |

Primary Examiner—William E. Kamm
Assistant Examiner—Kennedy J. Schaetzle
Attorney, Agent, or Firm—O'Connor Cavanagh

[57] ABSTRACT

A pulse generator for a cardiac pacemaker is adapted to be implanted beneath the skin and adjacent the musculus with either of its two sides facing the musculus and its other side facing outwardly of the patient's body, at the option of the implanting surgeon, according to the desired orientation of the receptacle of the header for connection of an electrode lead to the pulse generator, and at the same time avoiding the presence of spurious signals attributable to flexation of the adjacent musculus and twitching attributable to stimulation of the adjacent musculus during operation of the pulse generator when implanted. To that end, the entire surface of the case is coated with an electrically insulative, biocompatible film except along a portion of the edge of the case between its two major sides which is to serve as an anodal contact surface for stimulating and sensing cardiac activity of the patient.

14 Claims, 1 Drawing Sheet

CARDIAC PACEMAKER WITH UNIVERSAL COATING

BACKGROUND OF THE INVENTION

The present invention relates generally to artificial cardiac pacemakers, and more particularly to implantable cardiac pacemakers in which the pacemaker pulse generator case forms an anodal surface.

Cardiac pacemaker therapy has passed through several important developmental stages, including those which have increased the longevity of the devices, decreased their size, and made their functions more flexible. Improvements have extended also to freeing the devices of interference from external noise sources, which allows enhanced recognition of the intrinsic cardiac signals.

A common technique for reducing interference from external noise sources involves the use of bipolar electrodes, which enables sensing of the intrinsic heart rate between a pair of points in the heart. The magnitude of the average intrinsic rate ranges from 1.0 to 8.0 millivolts (mv). However, bipolar electrodes are not without disadvantages, primarily attributable to the existence of two electrical channels, which affect the fracture rate, ease of handling, and thickness of the electrode lead.

Unipolar electrodes have a thinner lead diameter, greater flexibility, and fewer complications than the bipolar versions, and find greater acceptance, especially in Europe. The unipolar electrodes employ an endocardial electrode positioned in the heart as one electrical pole, which is connected via an insulated helical conductor to the pacemaker circuitry and thence, to the implanted pulse generator case which acts as the second electrical pole. During stimulation of the heart, the case acts as the anode, and the endocardial electrode is the cathode.

In the infancy, of implantable cardiac pacemaker therapy, the pulse generator case was composed of metal such as stainless steel, titanium or alloys thereof, without any coating so that the case was completely electrically conductive.

A disadvantage of unipolar electrode systems, in addition to the greater antenna effect between the generator case and the endocardial electrode tip, is that muscle potential can produce an undesired effect. As a practical matter, flexation of the pectoral muscle, on which the pulse generator is typically implanted in the patient, can produce voltages of similar amplitude and frequency to the intrinsic cardiac signals. This interference is conducted through the pulse generator case, with a resulting undesirable and potentially dangerous influence on the pacemaker functions. The effects may include improper inhibition, and, in the dual chamber pacemakers, improper triggering and initialization of re-entry tachycardias.

Customarily, muscle produced improper triggering of the pacemaker is avoided by coating the entire pulse generator electrically conductive case with an electrically insulating material except for a small uncoated window which serves as the anodal electrode contact. The coating material is typically a thermoplastic polymer film known commercially as parylene, which is both biocompatible and an excellent electrical insulator. In the usual procedure, the posterior side of the case, meaning all parts facing the (inside) pectoral muscle, all side walls, and part of the anterior (frontal) side of the case are coated with parylene, and only a small part of the anterior side of the case is the anodal window that faces the (outside) fatty tissue.

This method greatly reduces muscle-induced interference, and has been clinically proven and implemented in many thousands of pacemakers.

A further advantage of the coating technique is that it avoids inappropriate stimulation of the pectoral muscle by pacing signals between the generator case and the endocardial electrode tip, and thus eliminates the otherwise annoying twitch of the pectoral muscle with each stimulation of the myocardial tissue.

A disadvantage of such a coating method is that the pulse generator cannot be inverted or "flipped" (i.e., turned over so that the normally posterior side of the case is facing front, toward the fatty tissue, and the anodal window is facing inward, toward the pectoral muscle, with header up as in the "normal" orientation) for implantation in the patient. Only by allowing such inversion can either the right side or the left side of the case be selected as the outlet for the connector and lead, with the header up.

This becomes increasingly significant with diminished size of pulse generators, and the standard 60 centimeter (cm) length of the electrode lead which must be sufficiently rolled up to fit the subcutaneous pocket formed in the patient for implantation of the generator. Standard pulse generators which allow the possibility of an electrode lead outlet on only one side often cause mechanical difficulties for the patient. it would be desirable to have the capability to conveniently implant the generator with the case inverted, i.e., turned over, in some patients so that the electrode lead exits the other side. This capability would be desirable in clinical practice not only to accommodate right or left pectoral implantation but in those instances where the device must be positioned behind the pectoral muscle.

It is a principal object of the present invention to provide a pulse generator with an electrically insulating coating covering all but a portion of the electrically conductive case, that allows for this freedom of positioning choice.

SUMMARY OF THE INVENTION

The premise of the present invention is that the side outlet of the electrode lead should not be a determinant for the orientation of implantation of an otherwise universally applicable pulse generator case.

Briefly, according to the invention the anterior (front) and posterior (back) sides of the case, addressed as it is normally oriented for implantation, are covered with an electrically insulative coating such as parylene, but the edge connecting those two sides is left at least partly uncoated. Thus, the edge or narrow side of the case remains an electrically conductive anodal contact surface. As a consequence of this coating pattern, the pulse generator can be implanted in the "normal" orientation, or, just as conveniently, in the inverse or reverse orientation, so that the generator case can be turned for left exit or right exit of the electrode lead, as desired, and implanted in the left or the right side of the patient's chest.

Moreover, the orientation of the case will not adversely affect the measures taken (i.e., coating of the case) to avoid muscle stimulation or muscle flexation induced potentials that otherwise interfere with proper sensing of cardiac signals by the pacemaker. Optimal orientation of the case is possible for implantation in all instances.

In clinical tests of pulse generators with the case coating pattern provided by the invention, the electrical contact surface on the narrow side of the case was found to serve as a sufficient anodal electrode surface for cardiac stimulation, even with small, pear-shaped cases having only 6.0 to 6.5 millimeter (mm) thickness and an average diameter of 4.0 cm. Further, the case not only allowed correct sensing of the intrinsic heart rate, but also enabled effective stimulation without increasing energy demand, when compared with pulse generators having the conventional coating pattern.

Dual chamber pacemakers often employ bipolar electrodes, but also require an anodal contact of the pulse generator case for timing and synchronization.

Tests conducted on patients implanted with pulse generators according to the invention demonstrated that the timing of the pacemaker software is not adversely affected in either unipolar or bipolar versions of the pacemaker, and that cross-talk which might otherwise be encountered during high pacing currents and could affect both pacing and sensing, did not occur.

Even pacing voltages of 7.5 V, which are rarely used in routine clinical practice, could not trigger improper stimulation of the patient's pectoral muscle. Different orientations of the pulse generator case in the body did not adverse;y affect electrical properties of the pacemaker, because of the almost symmetrical positioning of the conductive zone.

Therefore, it is another important object of the invention to provide a pulse generator for a cardiac pacemaker which is adapted to be implanted beneath the skin and adjacent the musculus with either of its two sides facing the musculus and its other side facing outwardly of the patient's body, at the option of the implanting surgeon, according to the desired orientation of the receptacle of the header for connection of an electrode lead to the pulse generator, and at the same time avoiding the presence of spurious signals attributable to flexation of the adjacent musculus and twitching attributable to stimulation of the adjacent musculus during operation of the pulse generator when implanted.

A related object is to coat the entire surface of the case with an electrically insulative, biocompatible film except along a portion of the edge of the case between its two major sides which is to serve as an anodal contact surface for stimulating and sensing cardiac activity of the patient.

Yet another object of the present invention to provide a method for coating the metal case of a stimulus generator with an electrically insulating layer in a way that will allow the generator to be implanted with either of its two major sides facing downward toward the center of the patient's body, at the option of the implanting surgeon.

BRIEF DESCRIPTION OF THE DRAWINGS

The above and still further objects, features, aspects and attendant advantages of the invention will be better understood from the ensuing description of a presently contemplated best mode of practicing the invention, with reference to presently preferred embodiments thereof, taken in conjunction with the accompanying drawings, in which.

DETAILED DESCRIPTION OF THE PREFERRED EMBODIMENT AND METHOD

Figure 1:
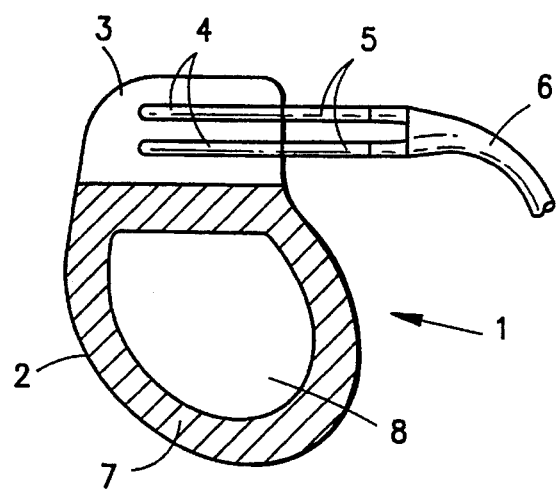
FIGS. 1, 2, and 3 are schematic illustrations of the front, back, and edge, respectively, of a pulse generator case according to the conventional coating methodology.
Figure 3:
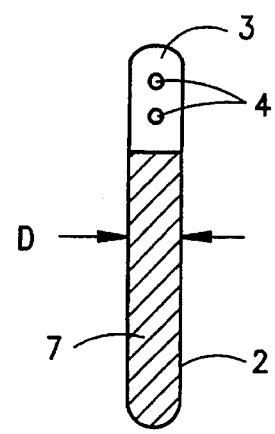
Figure 2:
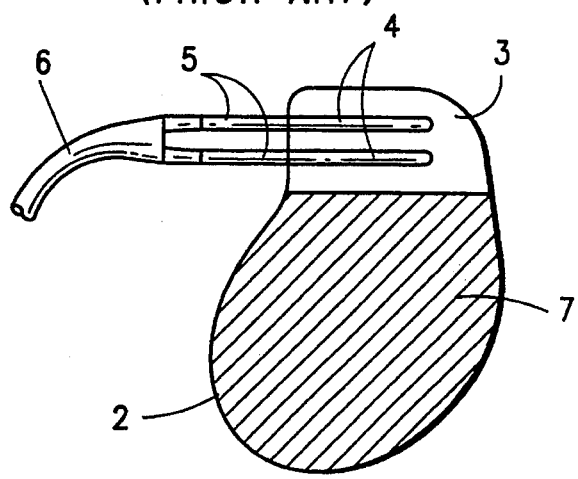

Referring to FIGS. 1, 2, and 3, a conventional pulse generator 1 for a cardiac pacemaker is adapted for implantation into a patient. The pulse generator may be a pacing device of any known type, single or dual chamber. It has an electrically conductive case 2 that houses the electronics for the generator. The case, which in this illustration is oval or slightly pear-shaped, is composed of a biocompatible metal such as titanium, and is hermetically sealed against intrusion of body fluids and tissue when implanted in the patient.

Atop the case is a header 3 composed of transparent epoxy resin, with receptacles 4 of the female portion of an electrical connector coupled in circuit to the internal electronics of the pulse generator. The male plugs 5 at the proximal end of an electrode lead 6 are adapted to be tightly inserted into the receptacles 4 for electrical connection therewith, and thus, with the circuitry of the generator. Lead 6 comprises an electrically conductive helical wire covered with an electrically insulative sheath and terminating at its distal end in an electrode to be positioned in a chamber of the patient's heart for electrical stimulation and/or sensing of cardiac activity. These elements of lead 6 and the device operation are completely conventional and are not depicted in the drawings, being unnecessary to an understanding of the invention.

For the sake of clarity of the description, FIG. 1 will be regarded as depicting the front side of the pulse generator case, and FIG. 2 the back side. FIG. 3 shows the narrow side, or edge, of case 2, and in this illustrative example, has a thickness D of, say, 6.0 mm. Typically, the pulse generator is implanted in a pocket surgically formed in the patient's flesh in the chest area, just beneath the skin. The "normal" orientation of the implanted device is with the back side (posterior) of the case facing the pectoral muscle, and the front side (anterior) facing the fatty tissue beneath the skin.

To avoid the aforementioned sensitivity to pectoral muscle-induced potentials and twitching caused by muscle stimulation, during operation of the implanted device, the case is coated by the manufacturer with a thin, electrically insulating layer 7 of parylene. The entire surface of the case 2 is coated—back side, front side, and connecting edge—except for a small centrally located portion or window 8 on the front side which serves as an uninsulated anodal contact surface for pacing. For purposes of illustration, the distance from the edge of the window to the edge of the case is about 6 mm.

If, for reasons of chest area implant location or orientation of the lead projecting from the case, the surgeon preferred to implant the device with the "front" side facing the pectoral muscle or inside of the patient, the location of the anodal contact surface would result in the spurious signal interference and muscle stimulation sought to be avoided by the very pattern of the case coating. In other words, the surgeon is foreclosed from exercising any option of choice of orientation of the generator, so far as inversion or "flipping" of the case is concerned.

Figure 4:
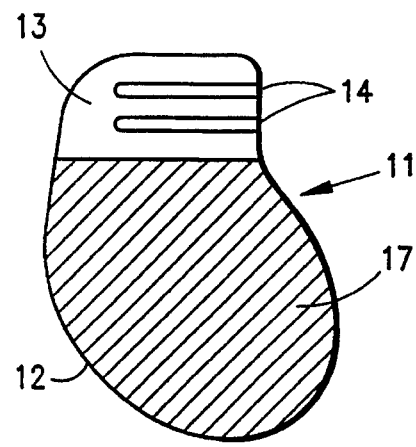
FIGS. 4, 5, and 6 are schematic illustrations of the front, back, and edge, respectively, of a pulse generator case according to the coating methodology of the present invention.
Figure 5:
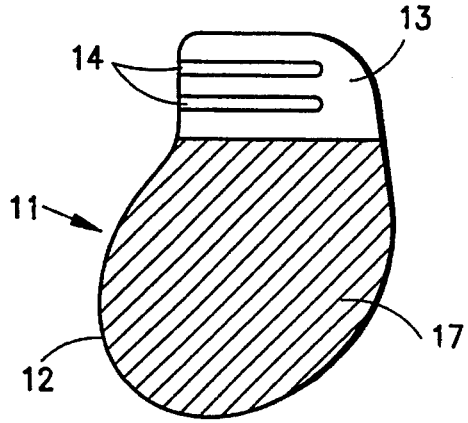
Figures 6, 7:
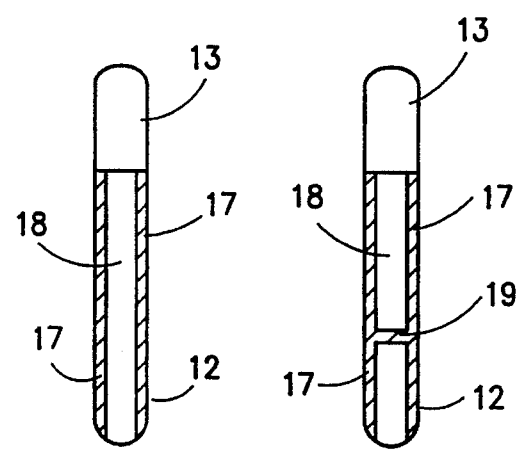
FIG. 7 is a schematic illustration of the edge of a pulse generator case according to a further embodiment of the present invention.

In the embodiment of the invention shown in FIGS. 4, 5, and 6, having the same relative orientations as the prior art device shown in respective FIGS. 1, 2, and 3, the shape of the case 12 of pulse generator 11 is the same as before, with a header 13 and receptacles 14. In the preferred embodiment of the insulative coating pattern according to the invention, however, the thin layer 17 of parylene covers the front and back sides of the case, but not at least a strip 18 of the edge of the case that connects the two sides. For a case having a thickness of 6 mm, the width of uncoated strip 18 is preferably a centrally located 4 mm so that approximately one mm on either side of the strip at the edge of the case is coated with parylene extending into the front and back sides of the case.

Strip 18 serves as the anodal window, which spans the entire edge of the case 12 from one end of the header 13 to the other, except for the slight overlap of coating at either side of the edge. If desired, the window may be interrupted at regularly spaced-apart intervals by coated bars 19, as illustrated in FIG. 7.

With this coating pattern, pulse generator case 12 may be implanted with either the back side or the front side facing the (inside) pectoral muscle tissue and the other side facing the (outside) fatty tissue. Thus, the electrode lead may exit from connector receptacles 14 at the right side of the device (FIG. 4) or the left side of the device (FIG. 5), whichever orientation of the case the implanting surgeon may prefer for the particular patient. In either instance, the pectoral muscle-induced spurious signal interference and pectoral muscle stimulation are avoided by virtue of the sufficiently remote location of the anodal contact surface relative to the muscle, as evidenced by the aforementioned clinical tests.

Implantation in a rotated position of the case 12 is also an option, as indicated by the double-headed arrows in FIGS. 4 and 5. In any event, the orientation of the anodal contact surface 18 remains the same. Although the layout pattern of the coating layer is shown for a non-symmetrical pulse generator case in the drawings, the pattern methodology of the present invention is applicable to symmetrical cases as well, including circular and U-shaped forms, for example.

Although the presently contemplated best mode of practicing the invention, and preferred embodiments and methods thereof, have been shown and described in this application, it will be apparent to those skilled in the art to which the invention pertains that variations and modifications of such embodiments and methods may be made without departing from the true spirit and scope of the invention. For example, the invention is not limited to pulse generators for cardiac pacemakers, but may extend to implantable stimulus generators for other medical devices intended for stimulation and/or sensing of body tissue, such as heart, nerves, muscles, and so forth. Accordingly, it is intended that the invention shall be limited only to the extent required by the appended claims and by application of the pertinent statutes and case law.

What is claimed is:

1. A pulse generator for a cardiac pacemaker adapted to be implanted beneath the skin and adjacent the musculus in the body of a patient, comprising an electrically conductive case having two sides and an edge connecting the two sides; a header projecting from the edge of the case for accepting a cathodic electrode lead in electrically connected relation to internal circuitry of the pulse generator within the case, and when so connected, the lead being restricted by the header to exit therefrom in a particular relative direction; and an electrically insulative layer coating the case everywhere except said edge in at least a portion thereof adapted to serve as an anodal contact surface for stimulation and sensing cardiac activity of the patient by the pulse generator; whereby the case may be implanted in the patient with either of said two sides facing the musculus and the other side facing outwardly of the patient's body according to the relative direction in which the lead is to exit from the header, while avoiding spurious signals attributable to flexation of the adjacent musculus and stimulation of the adjacent musculus during operation of the pulse generator when implanted.

2. The pulse generator of claim 1, wherein the uncoated portion of said edge runs along the entire surface of the case between said two sides.

3. The pulse generator of claim 2, wherein the coating layer extends at least slightly over said edge in a region adjacent to either of said two sides.

4. The pulse generator of claim 3, wherein the uncoated portion of said edge is interrupted by at least one strip of the coating layer connecting the coating layer on the two sides of the case.

5. The pulse generator of claim 1, wherein the coating layer is parylene.

6. A stimulus generator for a medical device adapted to be implanted in the body of a patient beneath the skin and adjacent the musculus to stimulate and sense electrical activity of preselected excitable body tissue by means of an electrode at the distal end of a conductive lead, comprising an electrically conductive case having two sides and an edge connecting the two sides; a header projecting from a portion of the edge of the case adapted for electrical connection of circuitry of the stimulus generator within the case to the proximal end of the lead; and an electrically insulative film coating the entire surface of the case except a portion of exposed surface of said edge adapted to serve as a complementary electrode contact surface for assisting said stimulation and sensing of electrical activity; whereby to allow implantation of the stimulus generator with either side of the case adjacent the musculus without danger of sensing or stimulating activity of the adjacent musculus during operation of the stimulus generator when implanted.

7. The stimulus generator of claim 6, wherein the uncoated portion of said edge runs along the entire surface of the case between said two sides.

8. The stimulus generator of claim 7, wherein the coating film extends at least slightly over said edge in a region adjacent to either of said two sides.

9. The stimulus generator of claim 8, wherein the uncoated portion of said edge is interrupted by at least one strip of the coating film connecting the coating film on the two sides of the case.

10. The stimulus generator of claim 6, wherein the coating film comprises parylene.

11. A method of electrically insulating the metal case of an implantable pulse generator for a cardiac pacemaker except for a limited surface area of the case adapted to serve as an anodic contact surface to assist in the stimulation and sensing of cardiac activity of a patient by the pulse generator, to enable the case to be implanted with either of its two sides facing pectoral muscle and the other side facing outwardly of the patient's body as desired for accommodating the direction in which an electrode lead adapted to be inserted into a header mounted on the edge of the case is to project from the header, while avoiding the presence of spurious signals attributable to flexation of adjacent pectoral muscle and muscle twitch attributable to stimulation of the adjacent pectoral muscle during operation of the pulse generator after implantation, the method comprising the steps of coating the entire surface of both sides of the case with a biocompatible, electrically insulating film while leaving only a major portion of the edge of the case between the two sides uncoated by said film to provide said anodic contact surface.

12. The method of claim 11, further comprising the step of restricting said major portion of the edge to a strip circumscribing the case and extending adjacent to but not touching either of said sides.

13. The method of claim 12, including the step of interrupting said strip by applying at least one band of the coating film across the strip to connect with the coating film on the two sides of the case.

14. The method of claim 11, including the step of applying parylene as the coating film.

* * * * *